United States Patent
Clark et al.

(10) Patent No.: US 11,202,747 B2
(45) Date of Patent: Dec. 21, 2021

(54) COMPOSITIONS WITH ACYLISETHIONATE SURFACTANT AND METHODS OF USE

(71) Applicant: Innospec Limited, Ellesmere Port (GB)

(72) Inventors: Peter Clark, Ellesmere Port (GB); Tony Gough, Chester (GB)

(73) Assignee: Innospec Limited, Ellesmere Port (GB)

( * ) Notice: Subject to any disclaimer, the term of this patent is extended or adjusted under 35 U.S.C. 154(b) by 0 days.

(21) Appl. No.: 16/091,368

(22) PCT Filed: Apr. 7, 2017

(86) PCT No.: PCT/GB2017/050984
§ 371 (c)(1),
(2) Date: Oct. 4, 2018

(87) PCT Pub. No.: WO2017/175005
PCT Pub. Date: Oct. 12, 2017

(65) Prior Publication Data
US 2019/0343747 A1    Nov. 14, 2019

(30) Foreign Application Priority Data
Apr. 8, 2016 (GB) .................................. 1606164

(51) Int. Cl.
| | | |
|---|---|---|
| A61K 9/00 | (2006.01) |
| A61K 8/46 | (2006.01) |
| A61K 8/41 | (2006.01) |
| A61K 8/73 | (2006.01) |
| A61K 8/892 | (2006.01) |
| A61Q 5/02 | (2006.01) |
| A61Q 5/12 | (2006.01) |

(52) U.S. Cl.
CPC .............. *A61K 8/466* (2013.01); *A61K 8/416* (2013.01); *A61K 8/731* (2013.01); *A61K 8/737* (2013.01); *A61K 8/892* (2013.01); *A61Q 5/02* (2013.01); *A61Q 5/12* (2013.01); *A61K 2800/10* (2013.01); *A61K 2800/20* (2013.01); *A61K 2800/5426* (2013.01); *A61K 2800/5428* (2013.01)

(58) Field of Classification Search
CPC ...................................................... A61K 8/466
See application file for complete search history.

(56) References Cited

U.S. PATENT DOCUMENTS

2015/0359722 A1    12/2015 Thomas et al.

FOREIGN PATENT DOCUMENTS

| | | |
|---|---|---|
| CN | 103251541 A | 1/2016 |
| EP | 2532344 A1 | 12/2012 |
| EP | 2605832 A1 | 6/2013 |
| EP | 2645986 A2 | 10/2013 |
| WO | 1994009763 A1 | 5/1994 |

(Continued)

OTHER PUBLICATIONS

International Search Report and Written Opinion dated May 29, 2017 for international application No. PCT/GB2017/050984 international filing date Apr. 7, 2017.

(Continued)

*Primary Examiner* — Paul W Dickinson
(74) *Attorney, Agent, or Firm* — Burns & Levinson LLP; Janine M. Susan

(57) ABSTRACT

A composition comprising: (a) an acyl isethionate surfactant; (b) a cationic polymer; and (c) a water insoluble benefit agent: wherein the composition comprises less than 3 wt % amphoteric or zwitterionic surfactants.

13 Claims, 2 Drawing Sheets

(56) References Cited

FOREIGN PATENT DOCUMENTS

| WO | 2004028482 A2 | 4/2004 |
| WO | 2005075623 A1 | 8/2005 |
| WO | 2007031793 A2 | 3/2007 |
| WO | 2012022553 A1 | 2/2012 |
| WO | 2012072424 A2 | 6/2012 |
| WO | 2014111668 A2 | 7/2014 |
| WO | 2015089259 A1 | 6/2015 |

OTHER PUBLICATIONS

United Kingdom Search Report dated Feb. 8, 2017, for Application No. GB1606164.0.
United Kingdom Combined Search and Examination Report dated Nov. 10, 2017, for Application No. GB 1705626.8.
International Preliminary Report on Patentability dated Oct. 18, 2018, for international application No. PCT/GB2017/050984.

COMPOSITIONS WITH ACYLISETHIONATE SURFACTANT AND METHODS OF USE

CROSS-REFERENCE TO RELATED APPLICATIONS

This application is a U.S. national stage application under 35 371 of International Application No. PCT/GB2017/050984 filed on Apr. 7, 2017, which in turn claims priority to GB Application No. 1606164.0 filed on Apr. 8, 2016, the contents of which are incorporated by reference herein in their entireties for all purposes.

BACKGROUND

The present application relates to compositions having cleansing and conditioning properties, especially personal care compositions.

In particular the present invention relates to hair care compositions having cleansing and conditioning properties. Combined shampoo and conditioner compositions are commonplace in the market and are favoured by the consumer as they allow the hair to be cleansed and conditioned using a single formulation, often termed a "2 in 1" formulation. This saves time and expense. However there can be issues in relation to the inclusion of certain surfactants in a single composition. For example there may be difficulties with the stability of formulations and achievement of desired properties of both cleansing and conditioning.

Conditioning compositions often comprise silicones. These are relatively expensive ingredients and it is desirable to minimise their concentration where possible and maximise the benefit obtained from these compounds. Many common commercially available 2 in 1 shampoo and conditioning compositions comprise sulfate based surfactants such as sodium lauryl ether sulfate. However there is a current desire amongst consumers for sulfate free compositions.

BRIEF SUMMARY

The present inventors have surprisingly found that particular combinations of components give unexpected benefits in combined cleansing and conditioning compositions.

DETAILED DESCRIPTION

Figure 1:
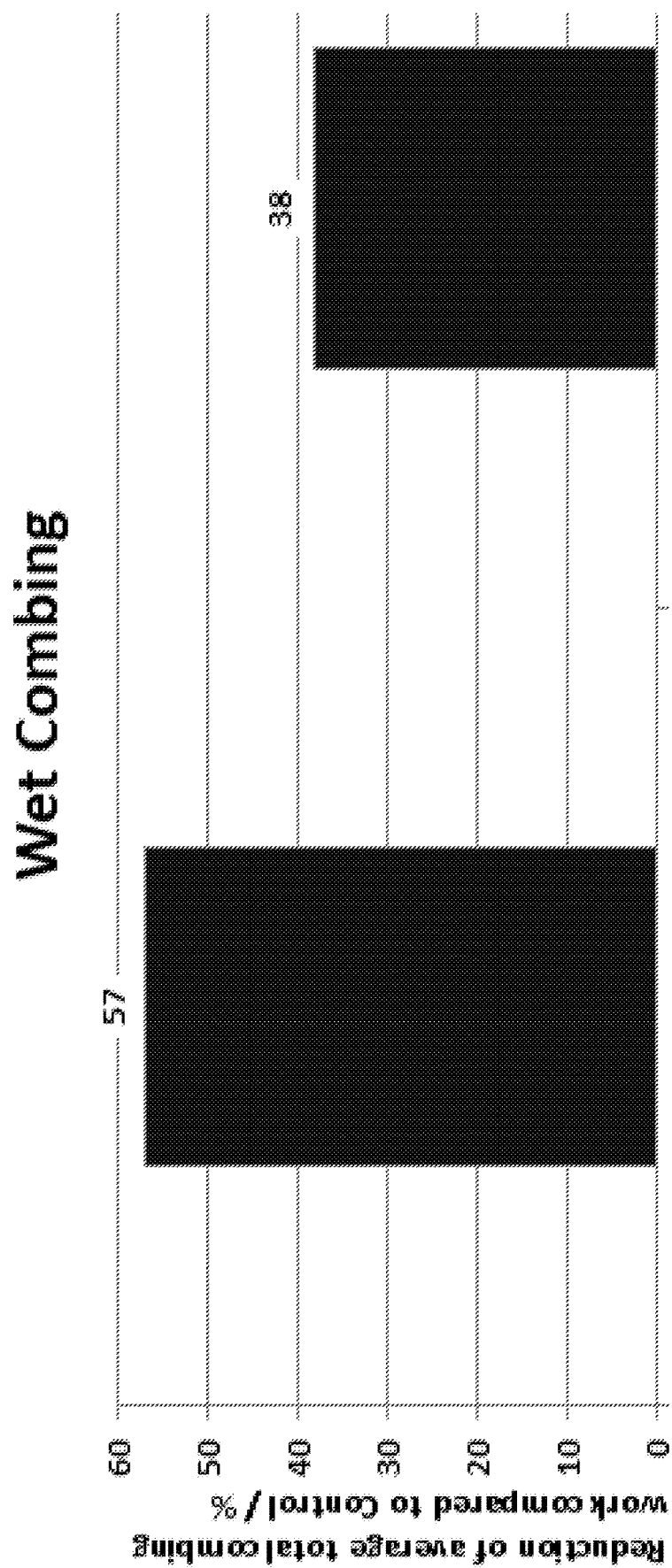
FIG. 1 shows the result of wet combing for shampoo formulation 1, according to the invention and comparative shampoo formulation 2.

According to a first aspect of the present invention there is provided a composition comprising:
(a) an acyl isethionate surfactant;
(b) a cationic polymer; and
(c) a water insoluble benefit agent;
wherein the composition comprises less than 3 wt % amphoteric or zwitterionic surfactants.

The compositions of the present invention comprise less than 3 wt % amphoteric or zwitterionic surfactants. By this we mean that the composition may comprise no amphoteric or zwitterionic surfactants (i.e. 0%) or it may comprise amphoteric or zwitterionic surfactants provided that the total amount of amphoteric or zwitterionic surfactants is less than 3 wt %.

Component (a) comprises an acyl isethionate surfactant.

The acyl isethionate surfactant is suitably selected from acyl isethionates of formula $R^6COOCH_2CH_2SO_3^-M^+$, alkyl acyl isethionates of formula (I):

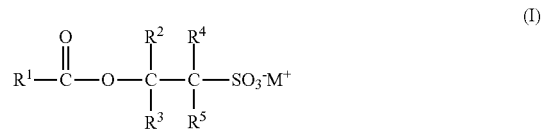

wherein $R^1$ and $R^6$ each independently represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation; and mixtures thereof.

Preferably $M^+$ represents an optionally substituted ammonium cation or, most preferably, a metal cation. Suitable ammonium cations include $NH_4^+$ and the ammonium cation of triethanolamine. Suitable metal cations include alkali metal cations, for example sodium, lithium and potassium cations, and alkaline earth metal cations, for example calcium and magnesium cations. Preferably $M^+$ represents a potassium cation, or, especially, a sodium cation.

The skilled person will appreciate that when $M^+$ is a divalent metal cation two moles of anion will be present for each mole of cation.

In some embodiments component (a) comprises an acyl isethionate of formula $R^6COOCH_2CH_2SO_3^-M^+$.

$R^6$ is selected from a substituted or unsubstituted alkyl, alkenyl, aryl or alkylaryl group. More preferably $R^6$ is selected from a substituted or unsubstituted alkyl or alkenyl group. Most preferably $R^6$ is an unsubstituted alkyl or alkenyl group, especially an unsubstituted alkyl group.

Preferably $R^6$ represents a represents a $C_{4-36}$ alkyl group, suitably $C_{5-30}$ alkyl group, preferably a $C_{7-24}$ alkyl group, more preferably a $C_{7-21}$ alkyl group, most preferably a $C_{7-17}$ alkyl group.

Preferably the acyl isethionate surfactant of formula $R^6COOCH_2CH_2SO_3M^+$ is selected from sodium lauroyl isethionate, sodium cocoyl isethionate, sodium oleoyl isethionate and mixtures thereof.

More preferably the acyl isethionate surfactant of formula $R^6COOCH_2CH_2SO_3M^+$ is selected from sodium lauroyl isethionate, sodium cocoyl isethionate and mixtures thereof.

In some embodiments component (a) may comprise a mixture of acyl isethionate compounds of formula $R^6COOCH_2CH_2SO_3^-M^+$.

In some embodiments component (a) may comprise a mixture of one or more acyl isethionate compounds of formula $R^6COOCH_2CH_2SO_3M^+$ and one or more compounds of formula (I).

In preferred embodiments component (a) comprises a compound of formula (I):

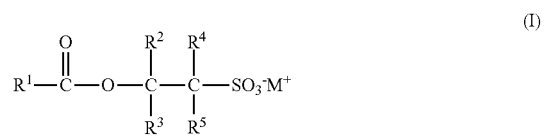

Preferably R¹ is selected from a substituted or unsubstituted alkyl, alkenyl, aryl or alkylaryl group. More preferably R¹ is selected from a substituted or unsubstituted alkyl or alkenyl group. Most preferably R¹ is an unsubstituted alkyl or alkenyl group, especially an unsubstituted alkyl group.

Preferably R¹ represents a 04.36 alkyl group, suitably $C_{5-30}$ alkyl group, preferably a $C_{7-24}$ alkyl group, more preferably a $C_{7-21}$ alkyl group, most preferably a $C_{7-17}$ alkyl group.

Preferably R² represents a $C_{1-4}$ alkyl group, suitably a $C_{1-4}$ alkyl group in which a propyl or butyl group, when present, is straight-chained. Preferably R² represents an n-propyl, ethyl or, most preferably, a methyl group.

Preferably R³ represents a hydrogen atom.

Preferably one of R⁴ and R⁵ represents a hydrogen atom and the other represents a hydrogen atom or a $C_{1-4}$ alkyl group. Preferably one of R⁴ and R⁵ represents a hydrogen atom or a $C_{1-4}$ alkyl group in which a propyl or butyl group is straight-chain. Preferably one of R⁴ and R⁵ represents an n-propyl, ethyl or methyl group or, most preferably, a hydrogen atom. Most preferably both R⁴ and R⁵ represent hydrogen atoms.

In some embodiments the present invention may include a mixture of more than one compound of formula (I). For example an isomeric mixture of compounds of formula (I) may be present. Such a mixture may include, for example a compound in which R² is alkyl (suitably methyl) and R³, R⁴ and R⁵ are all hydrogen and a compound in which R⁵ is alkyl (suitably methyl) and R², R³ and R⁴ are all hydrogen.

R¹ may be an alkyl group or an alkenyl group. Preferably R¹ is an alkyl group. In some embodiments the component surfactant of the present invention may comprise a mixture of fatty acids to form a mixture of compounds of formula (I) in which R¹ may be different.

R¹ is preferably the residue of a fatty acid. Fatty acids obtained from natural oils often include mixtures of fatty acids. For example the fatty acid obtained from coconut oil contains a mixture of fatty acids including $C_{12}$ lauric acid, $C_{14}$ myristic acid, $C_{16}$ palmitic acid, $C_8$ caprylic acid, and $C_{18}$ stearic and oleic.

R¹ may include the residue of one or more naturally occurring fatty acids and/or of one or more synthetic fatty acids. In some preferred embodiments R¹ consists essentially of the residue of a single fatty acid.

Examples of carboxylic acids from which R¹ may be derived include coco acid, butyric acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behinic acid, eruic acid, docosahexanoic lignoceric acid, naturally occurring fatty acids such as those obtained from coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof. Most preferably R¹ comprises the residue of lauric acid, that is a saturated fatty acid having 12 carbon atoms or the residue of mixed fatty acids derived from coconut oil.

The compound of formula (I) may be prepared by any of the methods disclosed in the prior art, for example see the methods described in WO94/09763 and WO2005/075623.

In especially preferred embodiments, R³, R⁴ and R⁵ are all hydrogen and R² is ethyl or, most preferably methyl.

In such preferred embodiments the compound of formula (I) comprises the reaction product of sodium methyl isethionate and a fatty acid, that is a compound of formula (II):

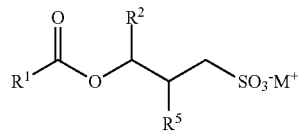

(II)

in which one of R² and R⁵ is methyl and the other is hydrogen. Mixtures of these isomers may be present.

Suitably such mixtures comprise approximately 90% of compounds which R² is methyl and R⁵ is hydrogen and approximately 10% of compounds in which R² is hydrogen and R⁵ is methyl.

In some embodiments the component (a) comprises one or more of sodium lauroyl methyl isethionate, sodium cocoyl methyl isethionate and sodium oleoyl methyl isethionate.

Most preferably the component (a) comprises sodium lauroyl methyl isethionate and/or sodium cocoyl methyl isethionate. Sodium lauroyl methyl isethionate is especially preferred.

Component (a) is suitably present in the composition of the first aspect of the present invention in an amount of at least 0.1 wt %, preferably at least 0.5 wt %, suitably, suitably at least 1 wt %, preferably at least 3 wt %, more preferably at least 5 wt %, suitably at least 6 wt %, for example at least 7 wt % or at least 8 wt %.

Component (a) may be present in the composition of the present invention in an amount of up to 40 wt %, suitably up to 30 wt %, preferably up to 20 wt %, more preferably up to 15 wt %, for example up to 13 wt % or up to 12 wt %.

Component (a) may comprise a mixture of compounds of formula $R_6COOCH_2CH_2SO_3M^+$ and/or a mixture of compounds of formula (I). In such embodiments the above amounts refer to the total amount of all such compounds present in the composition.

In some embodiments component (a) comprises a mixture of compounds of formula $R^6COOCH_2CH_2SO_3M^+$ and a mixture of compounds of formula (I). In some embodiments the weight ratio of the compound of formula $R^6COOCH_2CH_2SO_3M^+$ to the compound of formula (I) is suitably from 20:1 to 1:50, preferably from 10:1 to 1:20, suitably from 5:1 to 1:10, for example from 2:1 to 1:5.

In some embodiments the compound of formula $R^6COOCH_2CH_2SO_3M^+$ may be present in the composition of the first aspect of the present invention in an amount of at least 0.1 wt %, preferably at least 0.5 wt %, suitably, suitably at least 1 wt %.

The compound of formula $R^6COOCH_2CH_2SO_3^-M^+$ may be present in the composition of the present invention in an amount of up to 40 wt %, suitably up to 30 wt %, preferably up to 20 wt %, more preferably up to 15 wt %, for example up to 10 wt %.

Component (a) may comprise a mixture of compounds of formula (I). In such embodiments the above amounts refer to the total amount of all such compounds present in the composition.

In some preferred embodiments component (a) comprises less than 50 wt % of compounds of formula $R^6COOCH_2CH_2SO_3^-M^+$, suitably less than 10 wt %, preferably less than 5 wt %, for example less than 1 wt %.

In some preferred embodiments component (a) consists essentially of compounds of formula (I).

In preferred embodiments the compound of formula (I) is suitably present in the composition of the first aspect of the present invention in an amount of at least 0.1 wt %, preferably at least 0.5 wt %, suitably, suitably at least 1 wt %, preferably at least 3 wt %, more preferably at least 5 wt %, suitably at least 6 wt %, for example at least 7 wt % or at least 8 wt %.

In preferred embodiments the compound of formula (I) may be present in the composition of the present invention in an amount of up to 40 wt %, suitably up to 30 wt %, preferably up to 20 wt %, more preferably up to 15 wt %, for example up to 13 wt % or up to 12 wt %.

Component (a) may comprise a mixture of compounds of formula (I). In such embodiments the above amounts refer to the total amount of all such compounds present in the composition.

In some embodiments the composition of the present invention comprises at least 5 wt %, preferably at least 7 wt %, more preferably at least 9 wt % of compounds of formula (I) and less than 3 wt %, preferably less than 1 wt %, suitably less than 0.25 wt % of compounds of formula $R^6COOCH_2CH_2SO_3M^+$.

In some embodiments the composition of the present invention comprises at least 5 wt %, preferably at least 7 wt %, for example at least 9 wt % of one or more compounds selected from sodium lauroyl methyl isethionate, sodium cocoyl methyl isethionate and sodium oleoyl methyl isethionate.

In some embodiments the composition of the present invention comprises less than 1 wt %, preferably less than 0.5 wt % of sodium cocoyl isethionate and/or sodium lauroyl isethionate.

Component (b) is a cationic polymer. Any suitable cationic polymer may be used. Preferred cationic polymers include multiple quaternary ammonium residues bonded to a polymeric backbone. Suitable cationic polymers include those known as polyquaterniums on the list of International Nomenclature for Cosmetic Ingredients (INCI list).

Preferred cationic polymers for use herein are polysaccharide compounds which have been functionalised with a cationic residue, such as quaternary ammonium group. Especially preferred cationic polymers are based on cellulose or guar gum. Suitably these polysaccharides are functionalised by reaction with an epoxide and a tertiary amine to form cationic quaternary ammonium residues along the chain of the polysaccharide. Compounds of this type will be known to the person skilled in the art.

Suitable cationic polymers for use herein include cationic (or cationised) derivatives of guar gum or cationic (or cationised) derivatives of cellulose whereby the cationic group in each case is a quaternary ammonium group where each of the three alkyl groups not forming a link to the polymer back bone can be, independently from one another, one to thirty carbon atoms in length.

Especially preferred cationic polymers for use herein include guar hydroxypropyltrimonium chloride, hydroxypropyl guar hydroxypropyltrimonium chloride, and the cellulose based polymers known under the INCI names polyquaternium-24, polyquaternium-10 and polyquaternium-67.

Suitable Guar Hydroxypropyltrimonium Chloride polymers are available under the trade marks Activsoft C13 (Innospec), Activsoft C14 (Innospec), Activsoft C17 (Innospec), Activsoft CD (Innospec), Jaguar C-13-S(Solvay), Jaguar C-14-S(Solvay), Jaguar C-17 (Solvay), Jaguar Optima (Solvay), Jaguar C-500 Solvay and Jaguar C162 (Solvay).

Hydroxypropyl Guar Hydroxypropyl Guar Hydroxypropyltrimonium Chloride is available under the trade mark Jaguar C-162 (Solvay).

Polyquaternium-24 is available from Dow Chemical.

Polyquaternium-10 is available under the trade marks Condicare PQ10-4 (Innospec), UCARE Polymer JR400 (Dow Chemical) and UCARE Polymer JR 125 (Dow Chemical).

Polyquaternium-67 is available as Softcat SK series (Dow Chemical).

Other suitable cationic polymers will be known to the person skilled in the art.

Suitably component (b) may be present in the composition of the present invention in an amount of at least 0.01 wt %, suitably at least 0.05 wt %, preferably at least 0.1 wt %, more preferably at least 0.2 wt %, more preferably at least 0.25 wt %.

Suitably the cationic polymer may be present in an amount of up to 20%, suitably up to 10 wt %, preferably up to 5 wt %, more preferably up to 3 wt %, suitably up to 2 wt %, preferably up to 1 wt %, for example up to 0.8 wt %, up to 0.6 wt % or up to 0.5 wt %

Compositions of the present invention may comprise a mixture of two or more cationic polymers. In such embodiments the above amounts refer to the total amount of all cationic polymers present in the composition.

Suitably the weight ratio of component (a) to component (b) is at least 2:1, suitably at least 5:1, preferably at least 8:1, more preferably at least 10:1, for example at least 12:1 or at least 15:1.

The composition of the first aspect of the present invention comprises (c) a water insoluble benefit agent.

The water insoluble benefit agent may be selected from any material which gives a conditioning or other benefit to keratinous materials such as skin or hair. Suitable water insoluble benefit agents include natural or synthetic hydrocarbon based oils, vegetable oils, other emollient ester oils, silicones and perfluoro compounds, water insoluble anti-dandruff agents such as zinc pyrithione, sulfur or selenium sulfide; or water insoluble anti-bacterial/anti-microbial agents.

Preferably component (c) is a silicone compound. Preferred silicone compounds are silicone conditioning agents. Such compounds are known to the person skilled in the art.

Suitable silicone compounds include diphenylsiloxy phenyl trimethicone, phenyl trimethicone, trimethylsiloxyphenyl dimethicone, phenyl propyl dimethyl siloxysilicate, diphenyl dimethicone and bisphenylpropydimethicone, dimethicone, dimethiconol and divinyldimethicone/dimethicone copolymer.

Component (c) is suitably present in the composition in an amount of at least 0.1 wt %, suitably at least 0.5 wt %, preferably at least 1 wt %, suitably at least 1.5 wt %, more preferably at least 2 wt %, preferably at least 2.5 wt %, for example at least 2.7 wt % or at least 2.8 wt %.

Component (c) may be present in the composition in an amount of up to 20 wt %, suitably up to 15 wt %, preferably up to 10 wt %, more preferably up to 8 wt %, preferably up to 7 wt %, suitably up to 6 wt %, preferably up to 5 wt %, for example up to 4 wt %, up to 3.5 wt % or up to 3.2 wt %.

The composition of the first aspect may comprise a mixture of two or more silicone compounds. In such embodiments the above amounts refer to the total amount of all such components present in the composition.

Suitably the weight ratio of component (a) to component (c) is at least 1.5:1, suitably at least 2:1 preferably at least 3:1, suitably at least 4:1.

The compositions of the present invention may comprise one or more additional surfactants, for example one or further anionic surfactants, one or more cationic surfactants, one or more nonionic surfactants or one or more amphoteric or zwitterionic surfactants.

The composition of the present invention comprises less than 3 wt % amphoteric or zwitterionic surfactants. For the avoidance of doubt by this we mean that the total amount of all such surfactants present in the composition is less than 3 wt %.

An advantage of the present invention is that the formation of a coacervate allows inclusion of lower levels of amphoteric or zwitterionic surfactants than may otherwise be used. This offers cost benefits.

In some embodiments the compositions are substantially free of amphoteric or zwitterionic surfactants. For example the composition may comprise less than 1 wt %, less than 0.1 wt % or less than 0.01 wt % amphoteric or zwitterionic surfactants.

In some preferred embodiments the composition of the present invention further comprises (d) one or more amphoteric or zwitterionic surfactants. Suitable amphoteric and zwitterionic surfactants will be known to the person skilled in the art.

By amphoteric or zwitterionic surfactant we mean to include any surfactants having the ability to exhibit both positive and negative sites. The optional amphoteric or zwitterionic surfactant component (d) may be selected from surfactants referred to as betaines, including sultaines (sulfobetaines), or other zwitterionic or amphoteric surfactants, for example those based on fatty nitrogen derivates.

Suitable amphoteric or zwitterionic surfactants for inclusion as component (d) may be selected from betaines, for example alkyl betaines, alkylamidopropyl betaines, alkylamidopropyl hydroxy sultaines, alkylamphoacetates, alkylamphodiacetates, alkylamphopropionates, alkylamphodipropionates, alkyliminodipropionates and alkyliminodiacetates.

Preferred acetate-based surfactants for use as component (d) include sodium lauroamphoacetate, disodium lauroamphoacetate and mixtures thereof.

Preferred betaine surfactants for use as component (d) include cocoamidopropyl betaine.

Preferred sultaine surfactants for use as component (d) include cocoamidopropylhydroxy sultaine.

Most preferably component (d) comprises cocoamidopropylbetaine.

Component (d) is suitably present in an amount of at least 0.1 wt %, preferably at least 0.5 wt %, preferably at least 1 wt %, more preferably at least 1.5 wt % for example at least 1.75 wt % or at least 2 wt %.

Component (d) may be present in an amount of up to 2.95 wt %, suitably up to 2.9 wt %, preferably up to 2.8 wt %, more preferably up to 2.7 wt %, for example up to 2.6 wt %.

In some preferred embodiments the present invention provides a composition comprising:
(a) an acyl isethionate surfactant;
(b) a cationic polymer;
(c) a water insoluble benefit agent; and
(d) an amphoteric or zwitterionic surfactant.

In some preferred embodiments the composition of the present invention comprises:
(a) at least 5 wt %, preferably at least 8 wt % or a compound of formula (I);
(b) a cationic polymer based on cellulose or guar gum;
(c) a silicone conditioning agent; and
(d) from 0.1 to 3 wt %, preferably from 0.5 to 3 wt % of a zwitterionic or amphoteric surfactant.

In some preferred embodiments the composition of the present invention comprises:
(a) at least 5 wt %, preferably at least 8 wt % or a compound of formula (I);
(b) a cationic polymer based on cellulose or guar gum;
(c) a silicone conditioning agent; and
(d) from 0.1 to 3 wt %, preferably from 0.5 to 3 wt % of a zwitterionic or amphoteric surfactant;
wherein the composition comprises less than 2 wt %, preferably less than 0.5 wt % of compounds of formula $R^6COOCH_2CH_2SO_3M^+$.

In some embodiments the composition of the present invention comprises:
(a) at least 5 wt %, preferably at least 8 wt % or one or more compounds selected from sodium lauroyl methyl isethionate, sodium cocyl methyl isethionate and sodium oleoyl methyl isethionate;
(b) a cationic polymer based on cellulose or guar gum;
(c) a silicone conditioning agent; and
(d) from 0.1 to 3 wt %, preferably from 0.5 to 3 wt % of cocoamidopropylbetaine.

The composition of the present invention may include one or more further surfactants, for example one or more non ionic, cationic, or anionic surfactants.

Preferably any further surfactants are present in a total amount of less than 5 wt %, preferably less than 3 wt %, preferably less than 1 wt %.

Suitably component (a) and component (d) together comprise at least 70 wt % of all surfactant compounds present in the composition, preferably at least 80 wt %, suitably at least 90 wt %, suitably at least 95 wt %.

In some preferred embodiments the compositions of the present invention do not comprise significant proportions of any other anionic surfactants other than component (a).

In some embodiments component (a) preferably provides at least 50 wt % of all anionic surfactants present in the composition, preferably at least 70 wt %, preferably least 80 wt %, more preferably 90 wt %, and most preferably at least 95 wt % of all anionic surfactants present in the composition.

In some preferred embodiments the composition of the present invention comprises less than 5 wt % of anionic surfactants other than those provided in component (a), preferably less than 3 wt %, more preferably less than 1 wt %, preferably less than 0.5 wt %.

Preferably the composition of the present invention comprises less than 3 wt % of sulfate surfactants, preferably less than 1 wt %, more preferably less than 0.5 wt %, preferably less than 0.1 wt %, preferably less than 0.01 wt %. Preferably the compositions of the present invention are substantially free of sulfate based surfactants.

Preferably the compositions of the present invention comprise less than 3 wt % of anionic amide surfactants, preferably less than 1 wt %, preferably less than 0.5 wt %, preferably less than 0.1 wt %, preferably less than 0.01 wt %. In some preferred embodiments the compositions of the present invention are substantially free of anionic amide surfactants.

In some preferred embodiments the compositions of the present invention comprise less than 1 wt % of acrylamide containing polymers or copolymers, preferably less than 0.5 wt %, more preferably less than 0.1 wt %, preferably less than 0.01 wt % and most preferably less than 0.001 wt %.

Preferably the compositions of the present invention do not comprise less than 1 wt % zinc salts, preferably less than 0.5 wt %, preferably less than 0.1 wt % and more preferably less than 0.01 wt %.

For the avoidance of doubt the amounts of any component mentioned in this specification refer to the amount of active compound. However as the skilled person will appreciate components such as surfactants may be incorporated into the composition in a form which includes a diluent or carrier Suitably the composition of the present invention has a pH of from 4 to 8, preferably from 4.5 to 7, suitably from 4.5 to 6.5. For example 5.5 to 6.5 or from 5.9 to 6.1. The pH can be adjusted, as needed, with either a base, for example sodium hydroxide or sodium carbonate and/or an acid for example citric acid, succinic acid, or phosphoric acid. Preferred pH adjusting agents are sodium hydroxide and citric acid.

The composition of the present invention may comprise one or more further components selected from conditioning agents, antibacterial agents, foam boosters, pearlisers, opacifiers, perfumes, dyes, colouring agents, preservatives, thickeners, proteins, polymers such as silicone polymers, phosphate esters, sunscreens, antidandruff agents, buffering agents, moisturisers such as fatty acid alkanolamides, silicone derivatives, cationic polymers, propylene glycol, glycerine, viscosity controlling agents such as methyl cellulose, and other additives which are usually used for cleansing and/or conditioning compositions.

In some especially preferred embodiments the composition of the present invention further comprises a rheology modifier, an opacifier, a preservative and a fragrance.

The composition of the present invention is suitably provided in the form of a viscous liquid, gel or paste. It is suitably not in the form of a solid.

The composition of the present invention is preferably an aqueous composition. In some embodiments the composition may comprise one or more further solvents in addition to water. Such suitable co-solvents may include polar compounds for example alcohols, glycols and the like.

However in preferred embodiments water is the major solvent present in the composition of the present invention and suitably comprises at least 80 wt % of all solvents present, preferably at least 90 wt %, more preferably at least 95 wt %.

Suitably the composition comprises at least 10 wt %, preferably at least 20 wt % water, more preferably at least 30 wt %, preferably at least 40 wt %, suitably at least 50 wt %, preferably at least 60 wt %, for example at least 70 wt % or at least 75 wt %.

Preferably the composition of the present invention comprises a coacervate. This is a result of electrostatic attraction between the cationic polymer and molecules of the anionic surfactant component (a), and is a well-known phenomenon to those skilled in the art. Without being bound by theory it is believed that the coacervate thus formed in the compositions of the present invention is solubilised by the excess surfactant present to form a stable, insoluble, homogeneous composition. Upon dilution in use, the coacervate becomes insoluble; thus precipitates, and has an attraction to keratinous substrates, namely hair, due to its overall cationic charge. The precipitated coacervate thus deposits onto the hair, and remains on the hair after rinsing. The coacervate is also able to entrap water-insoluble materials also present in the composition, such as silicones, and carry these onto the hair surface. These water-insoluble materials also reside on the hair after rinsing and provide a benefit such as conditioning to the hair. This process is also a well-known phenomenon to those skilled in the art. In the current invention it is believed that the surfactants of component (a) form coacervates which are surprisingly more effective at causing the deposition of material onto the hair than coacervates formed from standard surfactants such as sodium laureth sulfate.

The composition of the present invention preferred has cleansing and conditioning properties. By cleansing properties we mean that the composition helps lift soils from a material treated with the composition. By conditioning properties we mean that a material that has been treated with the composition has an improved feel, texture, handle, combability or manageability.

Suitably the cleansing and conditioning properties affect the surface of a material treated with a composition. Suitably the composition helps lift soils from the surface of the material and has a conditioning effect by altering the surface of the material. It may alter the material by forming a deposit or an attachment to the surface in some way.

The composition of the present invention is a cleansing and conditioning composition. Preferably it is a personal care composition. More preferably the composition is a hair treatment composition. Most preferably the composition is a hair cleansing and conditioning composition. Such compositions may be referred to as conditioning shampoos or 2 in 1 shampoo and conditioning products.

According to a second aspect of the present invention there is provided a method of treating a material, the method comprising contacting the material with a composition comprising:
(a) an acyl isethionate surfactant;
(b) a cationic polymer; and
(c) a water insoluble benefit agent;
wherein the composition comprises less than 3 wt % amphoteric or zwitterionic surfactants.

Preferred features of the second aspect of the present invention are as defined in relation to the first aspect. Further preferred features of the first and second aspects will now be further defined.

Suitably the method of the second aspect involves contacting the material with a composition of the first aspect.

Any suitable material may be treated according to the method of the second aspect of the present invention. Suitable materials include fabrics. The method may involve treatment of wool materials such as carpets.

In preferred embodiments the material is a keratinous material. Preferably in the method of the second aspect the composition is contacted with the skin and/or hair of a human or animal.

Preferably the method of the second aspect involves contacting the composition with the skin and/or hair of a human.

Most preferably the method of the second aspect is a method of treating human hair, especially human hair growing on the head.

In preferred embodiments the composition used in the method of the second aspect is a hair care composition. Suitably it is a composition which has shampoo and conditioning properties. Suitably such a composition is applied to wet hair, massaged into the hair and then rinsed from the hair.

Thus in preferred embodiments the second aspect of the present invention provides a method of treating hair, method comprising the steps of:
(i) wetting the hair;
(ii) contacting the hair with a composition comprising
(a) an acyl isethionate surfactant;
(b) a cationic polymer; and
(c) a water insoluble benefit agent; and
(iii) rinsing the composition from the hair.

Methods of treating hair for cleansing and conditioning purposes involving wetting the hair, contacting the hair with the cleansing and conditioning composition and rinsing the hair are commonplace and well known to the person skilled in the art.

Suitably step (i) involves wetting the hair with warm water. Suitably in step (b) the cleansing and conditioning composition is applied to the hair, spread throughout the hair and massaged into the hair. Without wishing to be bound by theory, it is believed that as the composition is spread onto and massaged into the hair it is mixed with water in the hair and this dilution of the composition acts to destabilise the composition. Suitably the composition comprises a coacervate which precipitates upon dilution that occurs due to massaging and rubbing into the wet hair and subsequent rinsing from the hair in step (c). It is believed that the precipitation of the coacervate begins in step (b) and continues in step (c). As the coacervate precipitates in the hair the water insoluble benefit agent is entrapped and deposited onto the hair and is not all washed away. Thus following the method of the present invention benefits agents are suitably left on the hair. Suitably the benefit agent provides a conditioning effect.

It has been surprisingly found that compositions according to the present invention provide significantly improved conditioning properties compared with equivalent compositions using a sulfate based surfactant in place of the isethionate surfactant of formula (I).

Suitably the present invention may provide a method of treating hair, the method comprising the steps of:
(x) providing a composition of the first aspect which comprises a coacervate; and
(y) contacting the composition with the hair.

Suitably the method involves a step (z) of rinsing the hair which is carried out after step (y). Step (y) suitably involves contacting the composition with wet hair.

Preferably the hair treated according to the method of the present invention has improved condition as measured by a combing force/work measuring device such as the Dia-Stron MTT175 with combing rig attachments.

The invention will now be further described with reference to the following non-limiting examples.

EXAMPLE 1

Figure 2:
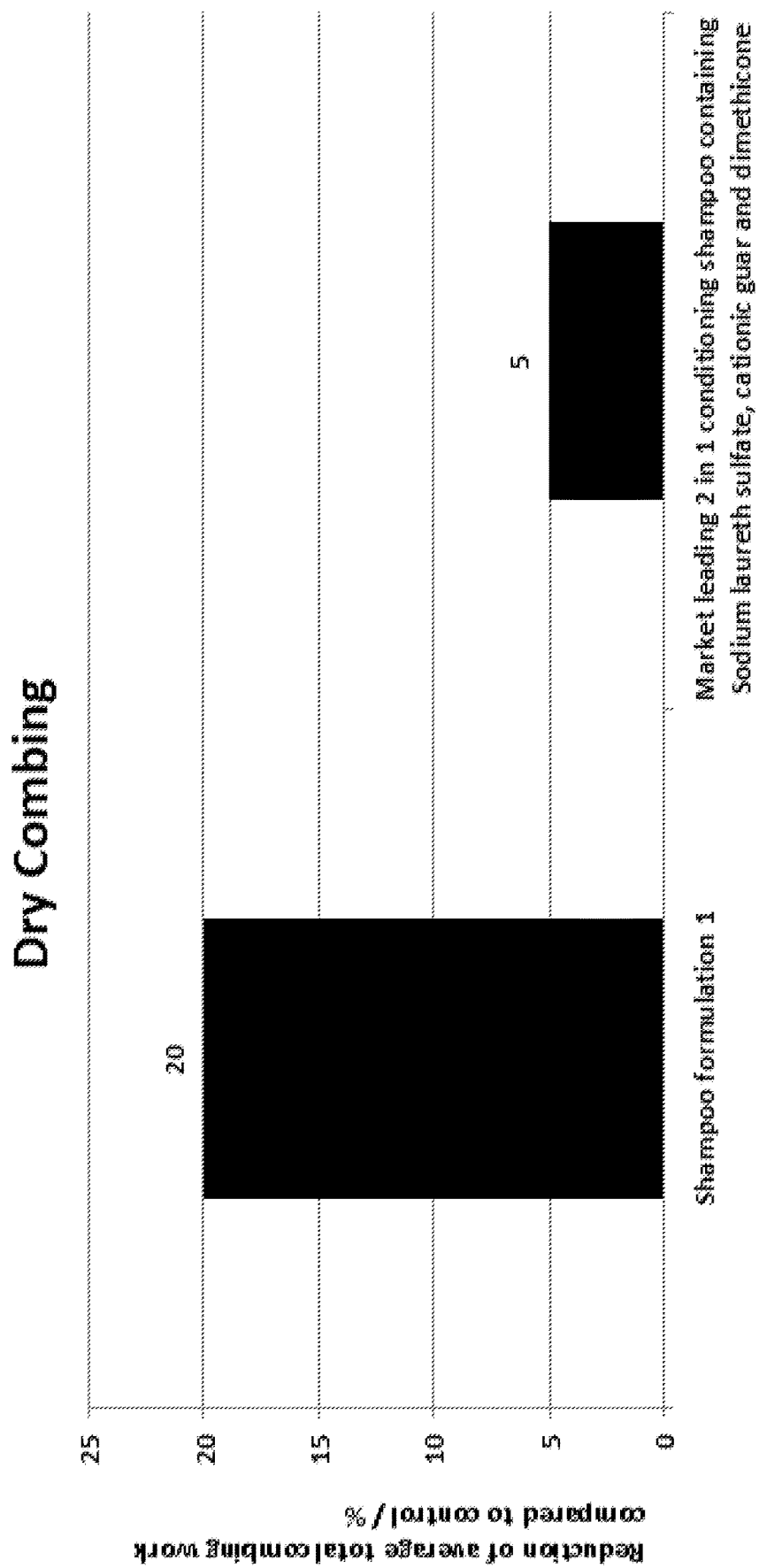
FIG. 2 shows the dry combing results of shampoo formulation 1 and a market leading 2 in 1 shampoo.

Hair shampoo formulations 1 and 2 shown in the table below were prepared according to the method shown. Clean bleached-hair tresses, each 18 cm in length and weighing 3 g (obtained from International Hair Importers, New York), were treated with 1 ml of shampoo according to the procedure given below and combing measurements were performed on them using a Dia-Stron MTT 175 with vertical stand and combing attachment set, attached to a personal computer with the Dia-Stron applications software installed. The averages of total work of combing for the shampoo treated tresses in the dry and the wet states were compared to the corresponding measurements for the control tresses which were not treated with the shampoos in the table below but just dipped in water. From this, the percentage reduction in the average total work of combing was calculated in each case. FIG. 1 shows the results of wet combing for shampoo formulation 1, according to the invention and comparative shampoo formulation 2. This shows that a sodium lauroyl methyl isethionate containing conditioning shampoo composition gave surprisingly superior wet combing improvement over a similar system which contained sodium laureth sulfate. FIG. 2 shows the dry combing results of shampoo formulation 1 and a market leading 2 in 1 shampoo based on sodium laureth sulfate and containing (inter alia) guar hydroxyproyl trimonium chloride and dimethicone.

Shampoo Formulation Compositions

| Ingredient (INCI name) | Amount in Formulation/% w/w * | |
|---|---|---|
| | Shampoo Formulation 1 | Shampoo Formulation 2 |
| Water | qs to 100 | qs to 100 |
| Carbopol (RTM) Silk 100 (Carbomer) | 0.60 | 0.60 |
| Iselux (RTM) LQ-CLR-SB (32%) (Sodium Lauroyl Methyl Isethionate) | 31.25 (10) | — |
| Steol SLES 2EO (27%) (Sodium Laureth Sulfate) | — | 37.04 (10) |
| Sodium Hydroxide | qs to pH 7.0 (at this addition stage) | qs to pH 7.0 (at this addition stage) |
| Tego (RTM) Betain F50 (37%) (Cocamidopropyl Betaine) | 6.58 (2.5) | 6.58 (2.5) |
| Emulsil DME-504 (Dimethicone (and) Laureth-4 (and) Laureth-23) | 3.00 | 3.00 |
| Aqua | 20.00 | 20.00 |
| Jaguar Excel (Guar hydroxypropyltrimonium chloride) | 0.40 | 0.40 |
| Opulyn PQG (Ethalkonium chloride acrylate/HEMA/styrene copolymer) | 1.00 | 1.00 |
| Water | 1.00 | 1.00 |
| Euxyl K100 (Benzyl Alcohol, Methylchloroisothiazolinone, Methylisothiazolinone) | 0.10 | 0.10 |
| Fragrance | 0.50 | 0.50 |
| Citric Acid | qs to pH 5.9-6.1 (Final pH) | qs to pH 5.9-6.1 (Final pH) |

* Numbers in brackets are active levels.

Method of Shampoo Formulation Preparation
1. Slowly add the Jaguar Excel to water with stirring until all the Jaguar excel dispersed then add 4 drops of citric acid solution to swell the polymer and mix for further 5 mins.
2. In separate vessel, slowly add the Carbopol Silk 100 in the remainder of the water with stirring and stir for c. 45 mins until all the polymer is dispersed.
3. To the mixture from (2) above, slowly add the surfactants and mix until uniform.
4. Adjust the pH of the mixture from (3) above to pH 7.0 with 25% w/w sodium hydroxide solution.
5. Slowly add Tego Betain F50 to the mixture from (4) above and mix until uniform.
6. Slowly add the mixture from (1) above to the mixture from (5) above and mix until uniform.
7. Slowly add Emulsil DME-504 to the resulting mixture and stir until uniform.
8. Add the Opulyn PQG, the Euxyl K100 and the Fragrance and mix until uniform.
9. Adjust the pH of final formulation to 5.9-6.1 with 50% citric acid solution.

Method of Shampoo Application to the Hair Tresses and Combing Evaluation
1. Wet the tress under warm tap water.
2. Apply 1 ml of the test formula to the hair tress and massage for 30 seconds.
3. Rinse the tress under the running water for 30 seconds.
4. Dry each tress using a hair dryer on a warm setting.
5. Hand comb each tress to remove any tangles.

6. Attach the top of the tress to the load cell of the Dia-Stron MTT 175 and place the hair into the teeth of the hard rubber comb attached to the moving bridge of the stand.
7. Perform the dry combing measurement.
8. Repeat the measurement/detangling procedure to produce five dry combing readings for each tress. (The result used is the average of the five readings).
9. Gently dip the tress in tap water three times and squeeze out excess water between the fingers down the length of the tress.
10. Perform the wet combing measurement as above to produce five wet combing readings.
(The result used is the average of the five readings).

The invention claimed is:

1. A composition comprising:
   (a) at least 9 wt % of compounds of formula (I):

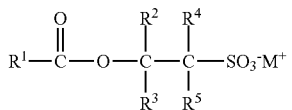

(I)

wherein $R^1$ represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation; and mixtures thereof;
   (b) a cationic polymer;
   (c) compounds of formula $R^6COOCH_2CH_2SO_3^-M^+$ in an amount of less than 0.25 wt % of the composition, wherein $R^6$ represents a $C_{4-36}$ substituted or unsubstituted hydrocarbyl group and $M^+$ represents a cation; and
   (d) a water insoluble agent which gives a conditioning benefit to keratinous materials;
   wherein the composition comprises less than 3 wt % amphoteric or zwitterionic surfactants.

2. The composition according to claim 1 wherein component
   (a) comprises one or more of sodium lauroyl methyl isethionate, sodium cocoyl methyl isethionate and sodium oleoyl methyl isethionate.

3. The composition according to claim 1 wherein component
   (b) is selected from cationic or catonised derivatives of guar gum or cationic or cationised derivatives of cellulose whereby the cationic group in each case is a quaternary ammonium group where each of the three alkyl groups not forming a link to the polymer back bone are, independently from one another, one to thirty carbon atoms in length.

4. The composition according to claim 1 wherein component
   (d) is a silicone compound.

5. The composition according to claim 1 wherein component
   (d) is selected from the group consisting of: dimethicone, dimethiconol and divinyldimethicone/dimethicone copolymer.

6. The composition according to claim 1 which comprises an amphoteric or zwitterionic surfactant.

7. The composition according to claim 1 which comprises no amphoteric or zwitterionic surfactant.

8. The composition according to claim 1 which comprises a coacervate.

9. A method of treating a material, the method comprising contacting the material with a composition comprising:
   (a) at least 9 wt % of compounds of formula (I):

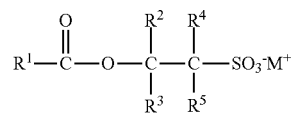

(I)

wherein $R^1$ represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation; and mixtures thereof;
   (b) a cationic polymer;
   (c) compounds of formula $R^6COOCH_2CH_2SO_3^-W$ in an amount of less than 0.25 wt % of the composition, wherein $R^6$ represents a $C_{4-36}$ substituted or unsubstituted hydrocarbyl group and $M^+$ represents a cation; and
   (d) a water insoluble agent which gives a conditioning benefit to keratinous materials;
   wherein the composition comprises less than 3 wt % amphoteric or zwitterionic surfactants.

10. The method according to claim 9 wherein the material is a keratinous material.

11. The method according to claim 10 wherein the material is human hair or animal hair.

12. A method of treating hair, the method comprising the steps of:
   (i) wetting the hair;
   (ii) contacting the hair with a composition comprising
      (a) at least 9 wt % of compounds of formula (I):

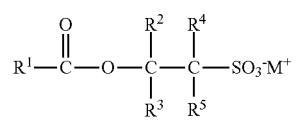

(I)

wherein $R^1$ represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation; and mixtures thereof;
      (b) a cationic polymer;
      (c) compounds of formula $R^6COOCH_2CH_2SO_3^-M^+$ in an amount of less than 0.25 wt % of the composition, wherein $R^6$ represents a $C_{4-36}$ substituted or unsubstituted hydrocarbyl group and $M^+$ represents a cation; and
      (d) a water insoluble agent which gives a conditioning benefit to keratinous materials; and
   (iii) rinsing the composition from the hair;
   wherein the composition comprises less than 3 wt % amphoteric or zwitterionic surfactants.

13. The method of treating hair, the method comprising the steps of:
   (x) providing a composition according to claim 1 which comprises a coacervate; and
   (y) contacting the composition with the hair.

* * * * *

UNITED STATES PATENT AND TRADEMARK OFFICE
CERTIFICATE OF CORRECTION

PATENT NO.         : 11,202,747 B2
APPLICATION NO.    : 16/091368
DATED              : December 21, 2021
INVENTOR(S)        : Peter Clark and Tony Gough Page 1 of 1

It is certified that error appears in the above-identified patent and that said Letters Patent is hereby corrected as shown below:

In the Claims

In Column 14, Line 19 of Claim 9:
"(c) compounds of formula $R^6COOCH_2CH_2SO_3^-W$"
Should read:
-- (c) compounds of formula $R^6COOCH_2CH_2SO_3^-M^+$ --

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*